United States Patent

Shiba

[11] 3,957,154
[45] May 18, 1976

[54] APPARATUS FOR ROTATING BOTTLES

[75] Inventor: Kikuo Shiba, Osaka, Japan

[73] Assignee: Hitachi Shipbuilding and Engineering Co., Ltd., Osaka, Japan

[22] Filed: Jan. 13, 1975

[21] Appl. No.: 540,589

[30] Foreign Application Priority Data

Jan. 29, 1974 Japan.............................. 49-12006
Jan. 31, 1974 Japan.............................. 49-13201

[52] U.S. Cl................................ 198/209; 198/257; 250/223 B
[51] Int. Cl.²....................................... B65G 29/00
[58] Field of Search .......... 198/209, 257, 258, 259, 198/260, 261, 283, 104; 250/223 B

[56] References Cited
UNITED STATES PATENTS

| | | | |
|---|---|---|---|
| 2,292,400 | 8/1942 | Nordquist | 198/209 |
| 2,880,845 | 4/1959 | Carter | 198/257 |

*Primary Examiner*—Evon C. Blunk
*Assistant Examiner*—Douglas D. Watts

[57] ABSTRACT

An apparatus for rotating bottles includes a circular turntable for transferring bottles from an inlet passage to an outlet passage along a circular arc. The bottles are maintained in position on the turntable by two pairs of superposed ratchet wheels which rotate with the turntable. A friction wheel is adapted to be brought into pressing contact with the body of a bottle on the turntable under the action of spring to rotate the bottle about its vertical axis. A cam causes the friction wheel to move at the same speed as the turntable through a specified angle of its rotation, following the rotation of the turntable, and to thereafter return to the original position. When returning to the original position, the friction wheel is moved away from the bottle by a hydraulic cylinder. While in pressing contact with the body of bottle, the friction wheel is rotated by a motor through an electromagnetic clutch.

11 Claims, 6 Drawing Figures

APPARATUS FOR ROTATING BOTTLES

BACKGROUND OF THE INVENTION

This invention relates to an apparatus for rotating bottles, more particularly to an apparatus for rotating bottles each about its vertical axis for the identification of a defective bottle or for labelling operation while the bottles are being successively transferred from an inlet passage to an outlet passage as arranged on the peripheral portion of a circular turntable.

Throughout the specification and claims, the term "inward" refers to a direction toward the center of turntable, while by the term "outward" is meant a direction away from the same center.

During the above-mentioned transfer operation, it is required to rotate each of the bottles automatically and smoothly about its vertical axis and, moreover, to maintain the bottle in a specified position on the turntable, for example, for the detection of a defective bottle.

SUMMARY OF THE INVENTION

The present invention provides an apparatus for rotating bottles which fulfils the foregoing requirements and which comprises a circular turntable rotatable to transfer bottles from an inlet passage to an outlet passage along a circular arc path as successively arranged on the peripheral portion of the turntable at predetermined spacing, means for holding the bottles in a specified position on the turntable while rendering each bottle rotatable about its vertical axis, and rotation imparting means for rotating the bottle itself on the turntable. While being transferred by the circular turntable, the bottles are subjected to the desired operation such as inspection. The bottle holding means, overcoming the force to impart rotation to the bottle, stably retains the bottle in position while rendering the bottle readily rotatable to thereby assure accurate inspection or reliable labelling operation.

This invention will be described below in greater detail with reference to the accompanying drawings.

DESCRIPTION OF THE PREFERRED EMBODIMENT

Figure 1:
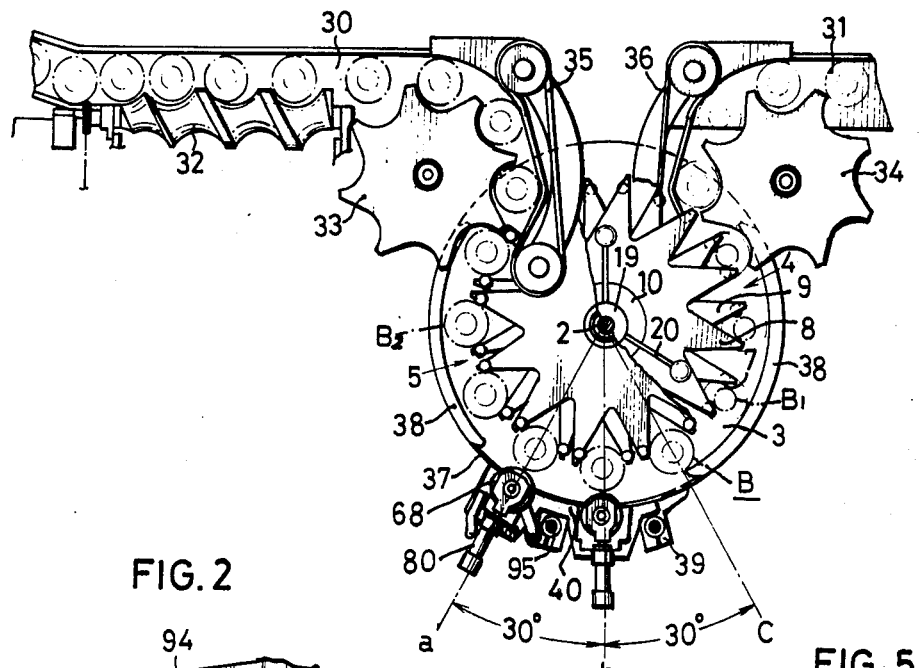
FIG. 1 is a plan view partly broken away and showing an embodiment of the bottle rotating apparatus according to this invention, with a frame omitted.
Figure 2:
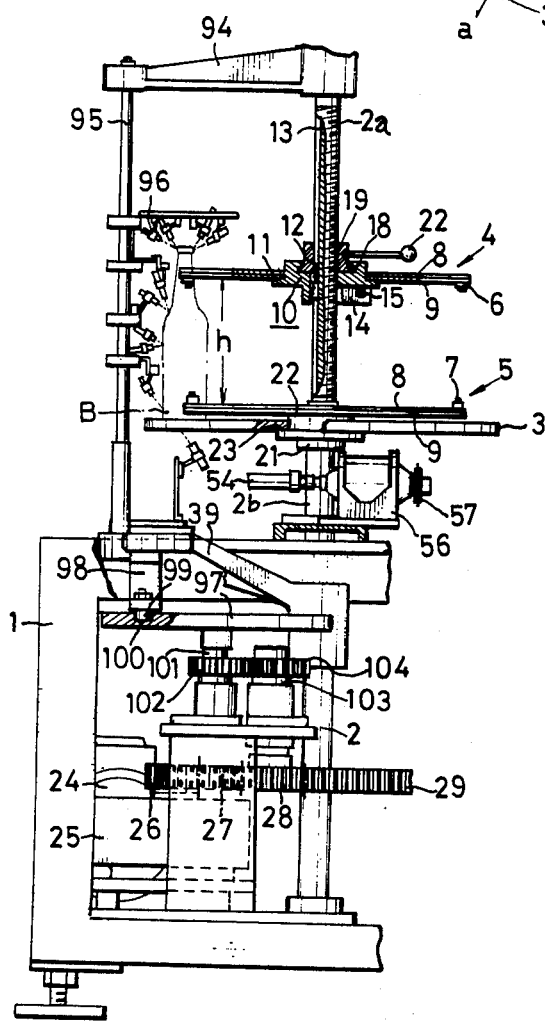
FIG. 2 is a side elevation partly broken away and showing the bottle rotating apparatus of FIG. 1.
Figure 3:
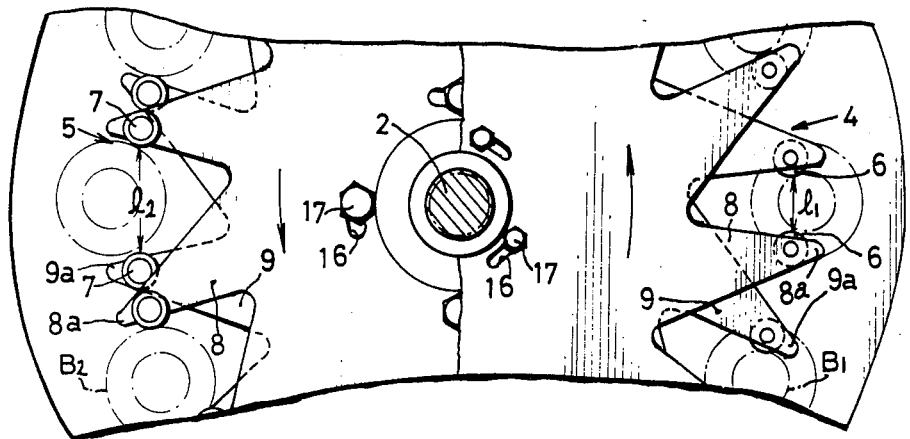
FIG. 3 is a fragmentary plan view on an enlarged scale showing holding members, part of bottle head holding member being broken away.

With reference to FIGS. 1 to 3, a rotary shaft 2 extends from the approximate center of bottom wall of a frame 1 and projects upward from the frame 1. The upper portion of the upward projection corresponding to about ¾ of the length thereof, is a male screw portion 2a, and the lower portion thereof, about ¼ of the length, is an unthreaded portion 2b. Fixed to the approximate upper end of the unthreaded portion 2b is a circular turntable 3 for carrying bottles B at predetermined spacing on its peripheral portion. A bottle head holding member 4 is positioned at the approximate middle of the screw portion 2a, and a bottle body holding member 5 at the upper end of the unthreaded portion 2b. Each of the holding members 4 and 5 comprises two ratchet wheels 8 and 9, with one superposed on the other. Each tooth of the ratchet wheels of the holding member 4 is provided at its end with a roller 6, whilst the holding member 5 likewise carries a roller 7 at the end of each tooth thereof. The teeth 8a of the ratchet wheel 8 extend in an opposite direction to the teeth 9a of the ratchet wheel 9. The former teeth 8a are out of register with the latter teeth 9a to provide spaces therebetween for receiving the bottles respectively. Nipping space $l_1$ determined by the distance between the adjacent rollers 6 on the upper and lower ratchet wheels 8 and 9 of the holding member 4 is slightly smaller than the diameter of bottle head $B_1$. Like nipping space $l_2$ between the adjacent rollers 7 on the holding member 5 is slightly smaller than the diameter of bottle body $B_2$. The upper rollers 6 are mounted on the lower side of the ratchet wheels 8 and 9, whereas the lower rollers 7 are mounted on the upper side of the ratchet wheels 8 and 9. Toothed discs having radial projections are usable in place of the ratchet wheels. The ratchet wheels 8 and 9 of the holding member 4 are fitted to the stepped portion 11 of an upper cylindrical support member 10 and fixed thereto by bolts 17 passed through arcuate slots 16 which are formed in the ratchet wheels 8 and 9 close to the center thereof. Mounted on the inner peripheral surface of the support member 10 is a key 12 which is slidably fitted in a groove 13 formed in the screw portion 2a longitudinally thereof. The support member 10 has at its lower end a bifurcated portion 14 which is tightly fitted around the threaded portion 2a by a fastening bolt 15, whereby the support member 10 is secured to the screw portion 2a. In the top portion of the support member 10 there is formed a circular cavity 18 having an enlarged bottom. A female screw member 19, screwed on the male screw portion 2a and having a flange and a handle 20, is rotatably fitted at its lower portion in the cavity 18 against escapement. A lower cylindrical support member 21 has two stepped portions 22 and 23, namely the upper and lower. In the same manner as the holding member 4, the ratchet wheels 8 and 9 of the holding member 5 are mounted on the upper stepped portion 22. The turntable 3 is fixed to the lower stepped portion 23. When it is necessary to alter the distance $h$ between the holding members 4 and 5 in accordance with the height of bottles, the fastening bolt 15 on the bifurcated portion 14 is loosened and the female screw member 19 is then turned by the handle 20 to shift the support member 10 axially of the rotary shaft 2 for the fine adjustment of the height of the support member 10. When there arises the necessity of altering each of the nipping spaces $l_1$ and $l_2$ of the holding members 4 and 5 in accordance with the diameter of the portion of bottle to be nipped, the bolts 17 are loosened to slightly turn at least one of the ratchet wheels 8 and 9 and to thereby shift one wheel relative to the other.

The output of a motor 24 is transmitted through reduction gear means 25, a gear 26 mounted on its shaft, transmission gears 27 and 28 to a gear 29 which is mounted on the rotary shaft 2, whereby the shaft 2 is driven at a constant speed. Arranged on one side of the turntable 3 are an inlet passage 30 and an outlet passage 31 each comprising a conveyor. The inlet passage 30 is provided with a timing screw 32 and a star wheel 33 adjacent thereto. The bottles B sent forward on the inlet passage 30 in a row of close arrangement are separated from each other by these means and placed onto the peripheral portion of the turntable 3 at predetermined spacing. The outlet passage 31 is provided with a star wheel 34 alone, by which the bottles B carried on the rotating turntable 3 along a circular arc path are transferred to the outlet passage 31. The bottles are thereafter sent to the next process as aligned on the outlet passage 31. Disposed beside the star wheels 33 and 34 are guides 35 and 36, each in the form of an endless belt, for pressing the bottles B against the star wheels 33 and 34 while they are being transferred from the inlet passage 30 to the turntable and from the turntable 3 to the outlet passage 31. Arcuate guide plates 38 are positioned, with a guide wire 37 interposed therebetween, above the turntable 3 along its periphery.

Figure 5:
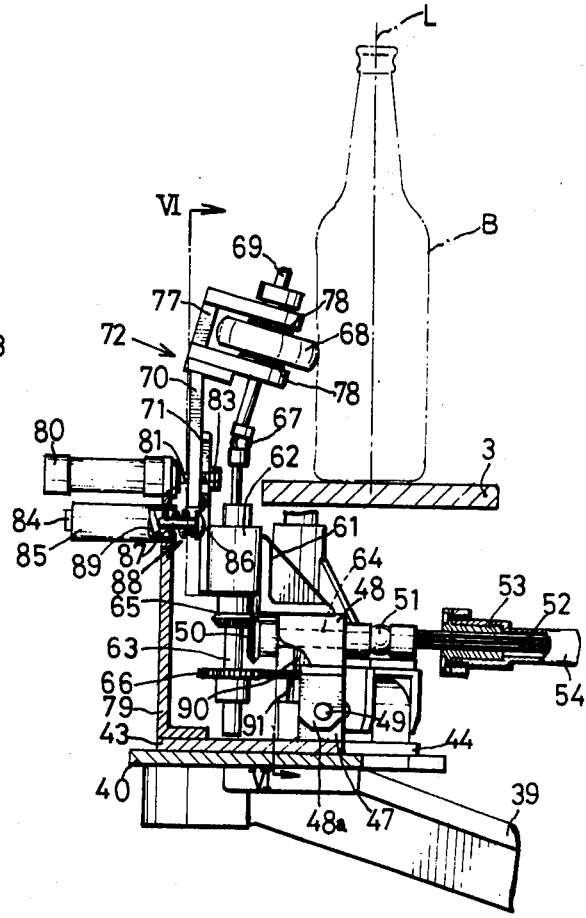
FIG. 5 is a view in section taken along the line V—V in FIG. 4.
Figure 6:
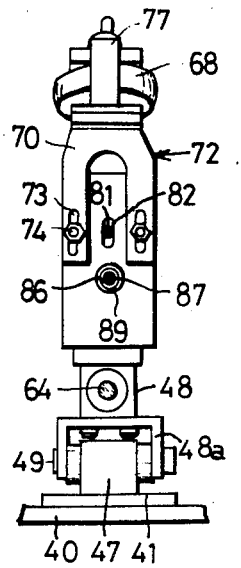
FIG. 6 is a view in section taken along the line VI—VI in FIG. 5.
Figure 4:
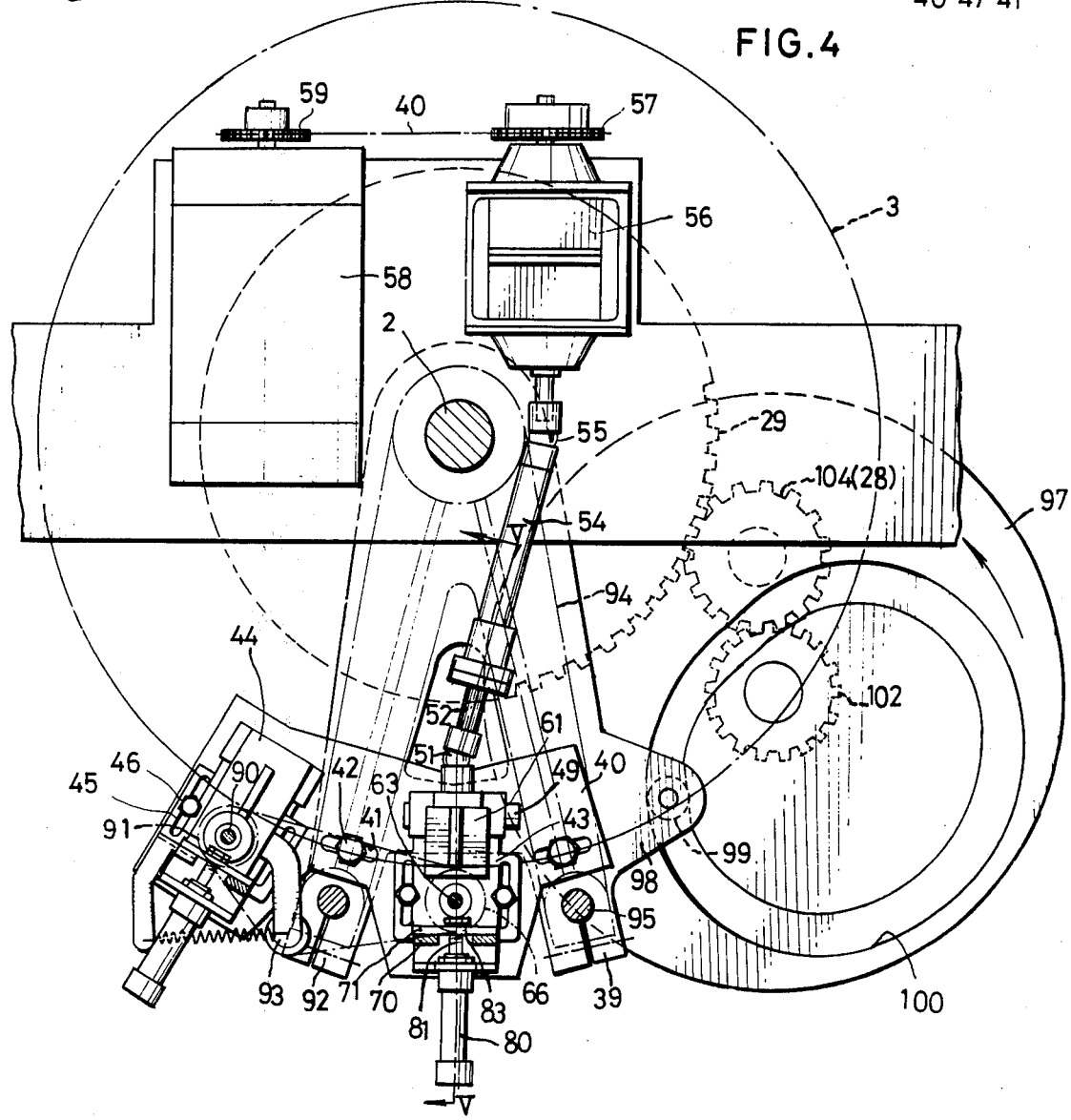
FIG. 4 is an enlarged plan view partly broken away and showing means for imparting rotation to bottles.

With reference to FIGS. 4 to 6, means for imparting rotation to bottles includes a horizontally pivotable member 39 which is pivoted to the rotary shaft 2 at an upper position in the interior of the frame 1. A base plate 40 is mounted on the distal end of the pivotable member 39 by bolts 42 passed through two arcuate slots 41 formed in the base plate. The plate 40 is therefore adjustably shiftable circumferentially of the turntable 3. Two adjusting plates 43 and 44 are mounted on the base plate 40 by bolts 46 passed through slots 45 formed in the plates 43 and 44 so that the plates are shiftable radially of the turntable 3 for adjustment. The adjusting plate 43 has an upright portion 47, to which is pivoted by a pin 49 an inverted U-shaped portion 48a extending downward from a horizontal bearing 48. A horizontal shaft 64 extends through and is supported by the bearing 48. A bevel gear 50 is mounted on the outward end of the shaft 64, and the inward end thereof is connected by a ball joint 51 to a spline shaft 52. The spline shaft 52 is slidably inserted in a horizontal tube 54 having an outward end which is splined in its interior surface as at 53. The inward end of the horizontal tube 54 is connected by a ball joint 55 to an electromagnetic clutch 56 installed on the top wall of the frame 1. The electromagnetic clutch is replaceable by an automatic clutch of some other type. A sprocket 57 is mounted on the input shaft of the clutch 56. A motor 58 mounted on the top wall of the frame 1 has an output shaft carrying a sprocket 59. A chain 60 is reeved around the sprockets 57 and 59 to transmit the rotation of the motor 58 to the horizontal shaft 48. Fixed to the top of the horizontal bearing 48 is an angle member 61, to the vertical side of which a vertical bearing 62 is secured. A vertical shaft 63 extends through and is supported by the bearing 62 in suspended manner. Mounted on the portion of the shaft 63 extending downward from the bearing 62 are a bevel gear 65 meshing with the bevel gear 50 and a transmission sprocket 66. The top end of portion of the shaft 63 extending upward from the bearing 62 is connected by a ball joint 67 to an inclined shaft 69 supporting a friction wheel 68. The friction wheel 68 is covered with rubber over the peripheral surface thereof so as to effectively impart rotation to the bottle B when brought into pressing frictional contact therewith. A vertically pivotable member 72 comprises an upper plate 70 and a lower plate 71, the lower half portion of the latter being fixedly mounted on the outer side of the vertical bearing 62. The upper plate 71 is fastened to the upper half portion of the lower plate 71 by bolts 74 passed through vertical slots 73 formed in the lower portion of the plate 70 at the opposite sides thereof. The upper plate 70 is therefore vertically shiftable for adjustment.

The upper plate 70 has a central cutout portion 75 extending from its lower end and is fixedly provided at its upper end with a bracket 76 downwardly slanting toward the turntable 3 and fixedly supporting a U-shaped frame 77. The upper and lower portions of the frame 77 include bearings 78, respectively, which support the inclined shaft 69. Thus the friction wheel 68 is inclined downward for pressing contact with the bottle B. A support plate 79, positioned in parallel to the vertical pivotable member 72 outwardly thereof, extends upward from the adjusting plate 43. A horizontal hydraulic cylinder 80 mounted on the upper end of the support plate 79 has a piston rod 81, which extends through the cutout portion 75 of the upper plate 70 and an elongated aperture 82 in the lower plate 71. The distal end of the rod 81, positioned inward of the plate 71, has a head 83 engageable with the edge of the apertured part when the piston rod 81 is retracted. Disposed immediately below and in parallel to the hydraulic cylinder 80 is a tube 85 having a bottom closed with a plug 84 and an opening directed inward. The tube 85 is mounted on the support plate 79 and has a pushing member 88 including a convex head 86 projecting from the opening and a leg 87 extending from the head into the tube 85. By the action of a coiled spring 89 wound around the leg 87 and supported at its opposite ends by the plug 84 and the head 86, the pushing member 88 always biases the vertical pivotable member 72 inward, namely toward the turntable 3. The kinds and arrangement of the parts mounted on the adjusting plate 44 are substantially the same as those on the adjusting plate 43, except that the rotation of the vertical shaft 63 on the plate 43 is delivered through sprocket-chain means to like friction wheel 68 on the plate 44. More specifically, a chain 92 is reeved around the sprocket 66 on the vertical shaft 63 and a sprocket 91 on a vertical shaft 90 and is always held taut by tension means 93.

A bifurcated horizontally pivotable member 94 is pivoted to the upper end of the rotary shaft 2 in facing relation to the horizontally pivotable member 39. Both the horizontal pivotable members 39 and 94 are connected together by two vertical rods 95. A required number of photoelectric tube means 96 are mounted by brackets on the vertical rods 95 and on the lower pivotable member 39 as arranged in specified positions. The photoelectric tube means may be replaced by other detecting members. A grooved cam 97 is located below the lower pivotable member 39, which has a bracket 98 supporting a cam follower 99. The follower 99 is engaged in the groove 100 of the cam 97. A gear 102, mounted on a cam shaft 101, meshes with a gear 104 which is mounted on an upper portion of a shaft 103. On the shaft 103, the gear 28 is mounted in meshing engagement with the gear 29 on the rotary shaft 2. Accordingly, the cam 97 is rotatable in timed relation to the turntable 3. The rotation of the cam 97 causes the horizontal pivotable members 39 and 94 to move reciprocally about the rotary shaft 2 through an angle of 30°, this movement taking place where the wire guide 37 is disposed. It therefore follows that between the phantom lines a and b, and between phantom lines b and c, extending radially of the turntable 3 in FIG. 1, the two friction wheels 68 reciprocally move respectively. Within the range of 30°, the movement of the pivotal members 39 and 94 takes place at a precisely equal speed to the rotational speed of the turntable 3 in the same direction over the range of 22°, other than the initial and terminal 4° ranges where the pivotable members slow down for reversion.

When the horizontally pivotable members 39 and 94 move forward, the piston rod 81 of each hydraulic cylinder 80 is forced out, permitting the pushing member 88 to push the vertically pivotable member 72 and to hold the friction wheel 68 in pressing contact with the body of bottle B. While this contact is effected, the clutch 56 is maintained in engaged state to transmit the torque of the motor 58 to the friction wheel 68, with the result that the bottle B is rotated about its vertical axis L. When the horizontally pivotable members 39 and 94 are moved backward, the piston rod 81 of the hydraulic cylinder 80 is retracted, this causing the head 83 to engage the vertically pivotable member 72 and to pull the same outward about the pin 49 against the action of the spring 89. As a result, the friction wheel 68 is moved away from the bottle B, whereupon the rotation of the bottle B is stopped. Simultaneously with the retraction of the piston rod 81, the clutch 56 is disengaged to interrupt the transmission of torque to the friction wheel 68. In this way, by bringing the friction wheel 68 into and out of pressing contact with the bottle B and by intermittently rotating the wheel 68 only while it is in contact with the bottle B, the bottle B itself is rotated on the turntable 3 while travelling through the specified section. In the same manner as above, the bottles B placed onto the turntable 3 are rotated one after another.

The arrangement of photoelectric tube means 96 shown in FIG. 2 is employed when the apparatus of this invention is used for the inspection of bottles to identify a defective bottle. In this case, the bottles B are rotated at least one turn. A crack, chip or like flaw in a bottle, when detected by the photoelectric tube means 96, is memorized by memory means and, when the defective bottle reaches the star wheel 34, unillustrated sucking means captures the bottle and transfers the same to an unillustrated bottle removing table without allowing transfer of the bottle to the outlet passage 31. Thus defective bottles are identified for removal.

When the present apparatus is used for labelling operation, the arrangement of the photoelectric tube means is of course altered. If the bottle has an embossed pattern or graduations, the bottle must not be labelled on such marked portion. Since bottles are sent toward the labelling machine with the marked portion directed in random directions, it is necessary to orient all the bottles in a definite direction before labelling so that the marked portion will not face the labelling machine. For this purpose, the bottle B is rotated to permit the photoelectric tube means to detect the marked portion, whereupon the rotation of the bottle B is immediately stopped. The bottle in the stopped position is correctly oriented for labelling.

The apparatus according to this invention is of course usable for various applications other than those described above.

What is claimed is:

1. An apparatus for rotating bottles comprising a circular turntable rotatable to transfer bottles from an inlet passage to an outlet passage along a circular arc path as successively arranged on the peripheral portion of the turntable at predetermined spacing, means for holding the bottles in position on the turntable while rendering each bottle rotatable about its vertical axis, and at least one rotation imparting means for rotating a bottle on the turntable, the holding means comprising a bottle head holding member and a bottle body holding member mounted on the upwardly projecting portion of the rotary shaft of the turntable, each of the holding members being composed of two toothed disks with one superposed on the other as a pair and having a roller at the end of each tooth of the disks, the teeth of one toothed disk of the pair being out of register with the teeth of the other toothed disk to provide spaces therebetween for receiving the bottles respectively, the distance between the adjacent rollers on the upper and lower toothed disks of the bottle head holding member defining a nipping space which is slightly smaller than the diameter of bottle head, the distance between the adjacent rollers on the upper and lower toothed disks of the bottle body holding member defining a nipping space which is slightly smaller than the diameter of bottle body.

2. The apparatus for rotating bottles as set forth in claim 1 wherein the rotation imparting means comprises a friction wheel movable inward radially of the turntable into pressing contact with the body of bottle and retractable radially outwardly of the turntable, intermittently rotating means for rotating the friction wheel only while the wheel is in pressing contact with the bottle body, and a friction wheel supporting member movable at the same speed as the turntable through a specified angle of rotation of the turntable to follow its rotation and thereafter returnable to the original position.

3. The apparatus for rotating bottles as set forth in claim 1 wherein the bottle head holding member is vertically shiftable by height adjusting means in accordance with the height of the bottle to be held, and the upper and lower toothed disks of each of the holding members are shiftable relative to each other by nipping space adjusting means in accordance with the diameter of the portion of bottle to be held.

4. The apparatus for rotating bottles as set forth in claim 3 wherein the height adjusting means comprises a male screw portion formed in the rotary shaft, a female screw member screwed on the male screw portion and having a handle, and a support member rotatably engaging a female screw member and keyed to the rotary shaft in vertically movable manner, the support member having a bifurcated fastening portion, the upper and lower toothed disks being mounted at their center portions on the support member.

5. The apparatus for rotating bottles as set forth in claim 3 wherein the nipping space adjusting means comprises a support member for mounting the center portions of the upper and lower toothed disks at a specified position on the rotary shaft and bolts passed through arcuate slots formed in at least one of the disks to secure the disks to the support member.

6. The apparatus as set forth in claim 3 wherein each of the upper and lower toothed disks is a ratchet wheel and the teeth of one of the disks extend in an opposite direction to the teeth of the other disk.

7. An apparatus for rotating bottles comprising a circular turntable rotatable to transfer bottles from an inlet passage to an outlet passage along a circular arc path as successively arranged on the peripheral portion of the turntable at predetermined spacing, means for holding the bottles in position on the turntable while rendering each bottle rotatable about its vertical axis, a horizontally pivotable member disposed below the turntable and pivoted to the rotary shaft thereof, reciprocating means for moving the horizontally pivotable member at the same speed as the turntable through a specified angle of rotation of the turntable to cause the pivotable member to follow the rotation of the turntable and thereafter returning the pivotable member to the original position, vertically pivotable members movable inward and outward radially of the turntable and extending upward from a base plate fixedly mounted on the horizontally pivotable member, friction wheels each mounted on an upper portion of each of the vertically pivotable members, pressing and releasing means for holding the friction wheel in pressing contact with the bottle body for a specified period of time and thereafter moving the wheel away therefrom, and intermittent transmission means for intermittently transmitting a torque to the friction wheel.

8. The apparatus for rotating bottles as set forth in claim 7 wherein the reciprocating means comprises a cam rotatable in timed relation to the turntable and a cam follower fixed to the horizontally pivotable member.

9. The apparatus for rotating bottles as set forth in claim 7 wherein the intermittent transmission means comprises an inclined shaft supporting the friction wheel and inclined to bring the wheel into pressing contact with the bottle, a vertical shaft connected by a ball joint to the inclined shaft, a horizontal shaft operatively associated with the vertical shaft by bevel gears, a spline shaft connected by a ball joint to the horizontal shaft, a horizontal tube splined and having the spline shaft slidably inserted therein, an automatic clutch connected by a ball joint to the horizontal shaft, and sprocket-chain means for operatively associating a motor to the clutch.

10. The apparatus for rotating bottles as set forth in claim 7 wherein the pressing and releasing means comprises a support plate disposed outward of each of the vertically pivotable members, a pushing member horizontally mounted on the support plate and inwardly biasing the vertically pivotable member all the time by a spring, and a hydraulic cylinder mounted on the support plate and having a piston rod extending through a vertically elongated aperture formed in the vertically pivotable member, the piston rod having a head engageable with the apertured portion when the rod is retracted.

11. The apparatus for rotating bottles as set forth in claim 7 wherein another horizontally pivotable member is pivoted to the upper end of the rotary shaft in facing relation to the horizontally pivotable member, both the horizontally pivotable members being connected together by vertical rods, and a required number of detecting members are mounted on the vertical rods in specified positions.

* * * * *